(12) United States Patent
Berneth et al.

(10) Patent No.: US 6,388,796 B1
(45) Date of Patent: May 14, 2002

(54) ELECTROCHROMIC DEVICE HAVING IMPROVED LIGHT STABILITY

(75) Inventors: Horst Berneth; Ralf Neigl, both of Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/501,489

(22) Filed: Feb. 9, 2000

(30) Foreign Application Priority Data

Feb. 18, 1999 (DE) .......................................... 199 06 655

(51) Int. Cl.$^7$ ................................................. G02F 1/15
(52) U.S. Cl. ........................ 359/265; 359/267; 359/269; 252/583
(58) Field of Search ................................ 359/265, 583, 359/269, 270, 273, 275, 267; 252/582, 586, 583

(56) References Cited

U.S. PATENT DOCUMENTS

| | | | |
|---|---|---|---|
| 3,280,701 A | 10/1966 | Donnelly et al. ............... | 88/77 |
| 4,902,108 A | 2/1990 | Byker ......................... | 350/357 |
| 5,128,267 A | 7/1992 | Köcher et al. ................. | 436/92 |
| 5,140,455 A | 8/1992 | Varaprasad et al. ......... | 359/275 |
| 5,151,816 A | 9/1992 | Vsraprasad et al. ........ | 359/275 |
| 5,280,380 A | 1/1994 | Byker ......................... | 359/265 |
| 5,300,637 A | 4/1994 | Hatch et al. ................. | 518/162 |
| 5,322,680 A | 6/1994 | Beck et al. ................... | 428/71 |
| 5,340,503 A * | 8/1994 | Varaprasad et al. ......... | 252/583 |
| 5,567,360 A * | 10/1996 | Varaprasad et al. ......... | 252/583 |

FOREIGN PATENT DOCUMENTS

| | | |
|---|---|---|
| DE | 3917323 | 11/1990 |
| DE | 4435211 | 4/1995 |
| WO | 94-23333 | 10/1994 |
| WO | 97-30134 | 8/1997 |
| WO | 98-05736 | 2/1998 |

OTHER PUBLICATIONS

Ullmann's Encyclopaedia of Industrial Chemistry, vol. 8, pp. 621–623, (month unavailable) 1977, Electromechanical Displays.

Elektrokhimiya, pp. 24–28, (Translated from Elektrokhimiva, vol. 13, No. 1, pp. 32–37 Jan. 1977, Shelepin et al, Electrochromism of Organic Compounds 1. Electrochemical and Spectral Properties of a System Based on Methylviologen and 3–Ethyl–2–Benzothiazolone Azine.

(List continued on next page.)

*Primary Examiner*—Georgia Epps
*Assistant Examiner*—Tim Thompson
(74) *Attorney, Agent, or Firm*—Joseph C. Gil; Richard E. L. Henderson; Diderico van Eyl (57) ABSTRACT

The invention relates to an electrochromic device having
  (a) a pair of glass or plastic plates or plastic films wherein at least one such plate or film is provided on one side each with an electrically conductive coating, wherein
    (1) at least one such plate or film and its conductive coating is transparent,
    (2) the other such plate or film and its conductive coating is optionally mirrored,
    (3) the electrically conductive layer of one or both of the two plates or films is optionally divided into separate segments optionally provided with individual contacts, and
    (4) the plates or films are joined on the sides of their conductive coating by means of a sealing ring to form a volume; and
  (b) the volume formed by the two plates or films and the sealing ring is filled with an electrochromic medium containing certain dihydronaphthazines or dihydrophenazines.

9 Claims, 1 Drawing Sheet

OTHER PUBLICATIONS

Elektrokhimiya pp. 404–408, (Translated from Elektrokhimiya, vol. 13, No. 4, pp. 474–478, Apr. 1977, Moisture–Exchange Process in Hydrogen–Oxygen Cells with Capillary Membrane III. Nonstationary Processes During Load Connection O.S. Abramzon et al.

Elektrokhimiya, pp. 271–274, (Translated from Elektrokhimiya, vol. 14, No. 2 pp. 319–322 Feb. 1978, O.A. Ushakov et al, Electrochromism of Organic Compounds some Properties Of Two–Electrode Cells.

J. Amer. Chem. So., 79 (month unavailable) 1957, pp. 6178–6179, Gilman et al, The Direct Preparation of Some Dihydro and Other Phenazine Derivatives.

Topics in Current Chemistry, vol. 92, pp. 1–44 (month unavailable) 1980, Hünig et al. Two Step Reversible Redox Systems of the Weitz Type.

J. Am., Chem. Soc. 117. (month unavailable) 1995) pp. 8528–8535, Tormos et al. Dithiadiazafulvalenes–New Strong Electron Donors. Synthesis Isolation, Properties and EPR Studies.

J.C.S. Perkin II, (month unavailable) 1990, pp. 1777–1783, Bryce et al, Synthesis and Redox Behavior of Highly Conjugated Bis(benzo–1,3,–dithiole) and Bis(benzothiazole) Systems containing Aromatic Linking Groups: Model Systems for Organic Metals.

J. Org. Chem., 57, (month unavailable) 1992, pp. 1849–1855, Synthesis of Tripyridiniumyl propenyl Anions from Tripyridiniumylcyclopropanes and –cyclopropenes, Gerard A. Crispino et al.

J. Am. Chem. Soc., 99, Aug. 31, 1977, pp. 6120–6122, Michael Horner & Siegfried Hünig, Bicyclo[1.1.0]butanes. A New Synthetic Route and Valence Isomerizations.

Uehara K. et al: "Highly Retifying Organic Two–Lay Diodes Using the Interface Between 5–methyl–10–(4–methylbenzyl)– and 5–methyl–10–(4–methoxybenzyl)–5,10–dihydrophenazines and lightly doped poly(3–methylthiophene)" Thin Solid Films, Elsevier–Sequoia S.A. Lausanne, CH, Bd. 235, Nr. 1/2, Nov. 25, 1993, Seiten 10–12, XP000408742, ISSN: 0040–6900.

J. C. S. Perkin II, (month unavailable) 1990, pp. 1777–83, Bryce et al, Synthesis and Redox Behaviour of Highly Conjugated Bis(benzo–1,3,–dithiole) and Bis(benzothiazole) Systems containing Aromatic Linking Groups: Model Systems for Organic Metals.

Angew. Chem. 90 (month unavailable) 1978, pp. 927–938 (English translation attached) Mehrstufige organische Redoxysysteme–ein allgemines Strukturprinzip, Von Klaus Deuchert et al.

Advanced Materials, 3, pp. 225–236, Hünig et al, (month available) 1991, DCNQIs–New Electron Acceptors for Charge–Transfer Complexes and Highly Conducting Radical Anion Salts.

* cited by examiner

Figure 1

ELECTROCHROMIC DEVICE HAVING IMPROVED LIGHT STABILITY

BACKGROUND OF THE INVENTION

The present invention relates to an electrochromic device having improved light stability.

Electrochromic devices are already known, for example from D. Theis in *Ullmann's Encyclopaedia of Industrial Chemistry*, Vol. A 8, page 622 (Verlag Chemie, 1987), and WO-A 94/23333. A distinction is made between two basic types:

Type 1: full-area electrochromic devices;

Type 2: electrochromic display devices having structured electrodes.

Type 1 is used, for example, in electrically darkenable window panes or electricaly dimmable automobile mirrors. Such devices are disclosed, for example, in U.S. Pat. No. 4,902,108.

Type 2 is used in segment and matrix displays. Such display devices are proposed, for example, in DE-A 196 31 728. Devices of this type can be observed transmissively or, in the case of reflection, reflectively.

WO-A 94/23333 compares electrochromic materials having different constructions, but these are not used as display devices:

Construction a: the electrochromic substances are in the form of a fixed film or layer on the electrodes (see Ullmann, above).

Construction b: the electrochromic substances are deposited on the electrodes as a layer by the redox process (see Ullmann, above).

Construction c: the electrochromic substances remain permanently in solution.

For construction (a), the best-known electrochromic material is the tungsten oxide/palladium hydride pair.

For construction (b), viologens have been described as electrochromic substances. These devices are not self-erasing, i.e., the image produced remains after the current has been switched off and can be erased again only by reversing the voltage. Such devices are not particularly stable and do not allow a large number of switching cycles.

In addition, the cells constructed using tungsten oxide/palladium hydride in particular cannot be operated in transmitted light, but only reflectively, owing to light scattering at these electrochromic layers.

*Elektrokhimiya*, 13, 32–37 (1977), 13, 404–408, 14, 319–322 (1978), U.S. Pat. No. 4,902,108, and U.S. Pat. No. 5,140,455 disclose an electrochromic system of construction (c). An electrochromic cell built up from glass plates with a conductive coating contains a solution of a pair of electrochromic substances in an inert solvent.

The pair of electrochromic substances used is one electrochemically reversibly reducible substance and one reversibly oxidizable substance. Both substances are colorless or only weakly colored in the ground state. Under the action of an electric voltage, one substance is reduced and the other oxidized, both becoming colored. When the voltage is switched off, the ground state re-forms in the case of both substances, decolorization or a color lightening taking place.

$$RED_1 + OX_2 \rightleftharpoons OX_1 + RED_2$$

(colorless) (colored)
(low energy pair) (high energy pair)

U.S. Pat. No. 4,902,108 discloses that suitable pairs of redox substances are those in which the reducible substance has at least two chemically reversible reduction waves in the cyclic voltammogram and the oxidizable substance correspondingly has at least two chemically reversible oxidation waves.

According to WO-A 94/23333, however, such solution systems of construction (c) have serious disadvantages. Diffusion of the electrochromic substances in the solution causes fuzzy color boundaries and high power consumption in order to maintain the colored state, since the colored substances are permanently degraded by recombination and reaction at the opposite electrode in each case. Nevertheless, various applications have been described for such electrochromic cells of construction (c). For example, they can be formed as automobile rear-view mirrors which can be darkened during night driving by application of a voltage and thus prevent dazzling by the headlamps of following vehicles. See U.S. Pat. No. 3,280,701, U.S. Pat. No. 4,902,108, and EP-A 0435 689. Furthermore, such cells can also be employed in window panes or automobile sunroofs, where they darken the sunlight after application of a voltage. Likewise described is the use of such devices as electrochromic display devices, for example in segment or matrix displays having structured electrodes. See DE-A 196 31 728.

The electrochromic cells normally consist of a pair of glass plates, of which, in the case of the automobile mirror, one is mirrored. One side of these sheets is full-area coated with a light-transparent, electroconductive layer, for example, indium-tin oxide (ITO), where, in the case of display devices, this conductive coating is divided into electrically separated segments provided with individual contacts. These sheets are used to construct a cell by bonding them by means of a sealing ring with their electroconductively coated sides facing one another to form a cell. This cell is filled with an electrochromic liquid through an opening and the cell is tightly sealed. The two sheets are connected to a voltage source via the ITO layers.

The electrochromic devices described above generally exhibit sensitivity to light, in particular UV light. Electrochromic devices containing UV absorbers have therefore been described, for example, in U.S. Pat. No. 5,280,380.

Compared with the use of UV absorbers, the use of electrochromic compounds which inherently have better light stability would be advantageous.

Surprisingly, it has now been found that the use of certain dihydronaphthazines or dihydrophenazines results in improved light stability of the electrochromic device.

SUMMARY OF THE INVENTION

The invention accordingly relates to an electrochromic device comprising (a) a pair of glass or plastic plates or plastic films wherein at least one such plate or film (preferably both plates or films) is provided on one side each with an electrically conductive coating, wherein (1) at least one such plate or film and its conductive coating is transparent, (2) the other such plate or film and its conductive coating is optionally mirrored,

(3) the electrically conductive layer of one or both of the two plates or films is optionally divided into separate segments optionally provided with individual contacts, and (4) the plates or films are joined on the sides of their conductive coating by means of a sealing ring to form a volume; and (b) the volume formed by the two plates or films and the sealing ring is filled with an electrochromic medium comprising a pair of electrochromic substances $OX_2$ and $RED_1$, wherein (1) $OX_2$ is a reducible electrochromic substance, and (2) $RED_1$ is an oxidizable electrochromic substance represented by at least one of the formulas wherein
$R^{201}$ is aryl,
$R^{202}$ is alkyl, cycloalkyl, alkenyl, aralkyl or aryl,
B is a bivalent bridge,
m and n, independently of one another, are integers from 1 to 4, and
$R^{203}$ to $R^{206}$, independently of one another, are hydrogen, halogen, alkyl, alkoxy, cyano or aryl,
with the provisos that when m is at least 2, two adjacent $R^{203}$ together also optionally represent a bivalent —CH=CH—CH=CH— radical and when n is at least 2, two adjacent $R^{204}$ together also optionally represent a bivalent —CH=CH—CH=CH— radical.

DETAILED DESCRIPTION OF THE INVENTION

Such dihydrophenazines are disclosed, for example, by H. Gilman and J. J. Dietrich in *J. Amer. Chem. Soc.*, 79, 6178 (1957) or can be prepared analogously.

Preferred dihydronaphthazines and dihydrophenazines of the formulas (CC) to (CCIII) are those in which $R^{201}$ is $C_6$–$C_{10}$-aryl,
$R^{202}$ is $C_1$–$C_{12}$-alkyl, $C_3$–$C_7$-cycloalkyl, $C_2$–$C_{12}$-alkenyl, $C_7$–$C_{16}$-aralkyl, or $C_6$–$C_{10}$-aryl,
B is —$(CH_2)_p$—, —$(CH_2)$—$(O$—$CH_2)_q$—$O$—$CH_2$— or —$(CH_2)_r$—$C_6H_4$—$(CH_2)_s$—, where the $CH_2$ groups are optionally substituted by methyl,
$R^{203}$ to $R^{206}$, independently of one another, are hydrogen, halogen, $C_1$–$C_4$-alkyl, $C_1$–$C_4$-alkoxy, cyano, or $C_6$–$C_{10}$-aryl,
m and n, independently of one another, are integers from 1 to 4,
with the provisos that when m is at least 2, two adjacent $R^{203}$ together can also represent a bivalent —CH=CH—CH=CH— radical and when n is at least 2, two adjacent $R^{204}$ together can also represent a bivalent —CH=CH—CH=CH— radical,
p is an integer from 2 to 20, and
q, r, and s, independently of one another, are integers from 0 to 10.

Particularly preferred dihydronaphthazines and dihydrophenazines of the formulas (CC) to (CCIII) are those in which $R^{201}$ is phenyl (which can optionally carry up to three methyl, methoxy, chlorine, bromine, or cyano radicals),
$R^{202}$ is optionally branched $C_1$–$C_8$-alkyl, cyclopentyl, cyclohexyl, benzyl, phenethyl, phenylpropyl, or phenyl (where these radicals can optionally carry up to three methyl, methoxy, chlorine, bromine, or cyano radicals),
B is —$(CH_2)_p$—,
$R^{203}$ to $R^{206}$, independently of one another, are hydrogen, chlorine, bromine, methyl, ethyl, propyl, butyl, methoxy, ethoxy, cyano, or phenyl,
m and n, independently of one another, are integers from 1 to 2,
with the provisos that when m is at least 2, two adjacent $R^{203}$ together can also represent a bivalent —CH=CH—CH=CH— radical and when n is at least 2, two adjacent $R^{204}$ together can also represent a bivalent —CH=CH—CH=CH— radical, and
p is an integer from 2 to 10.

In very particularly preferred form, the electrochromic device according to the invention comprises an $RED_1$ of the formula (CC). Preference is given to dihydrophenazines of the formula (CC) in which $R^{201}$ is phenyl, $R^{202}$ is methyl, ethyl, propyl, butyl, phenylpropyl, or phenyl (particularly preferably phenyl), $R^{203}$ and $R^{204}$ are hydrogen, and m and n are 1.

In a similarly preferred manner, the electrochromic device according to the invention comprises an $RED_1$ of the formula (CCII). Preference is given to dihydrophenazines of the formula (CCII) in which $R^{202}$ is phenyl, B is —$(CH_2)_p$—, $R^{203}$ and $R^{204}$ are hydrogen, m and n are 1, and p is an integer from 2 to 6.

Besides electrochromic substances $RED_1$ of the formulas (CC) to (CCIII), the electrochromic device according to the invention comprises at least one electrochromic substance $OX_2$. However, it can also comprise further $RED_1$ and/or $OX_2$ substances.

Through selection of the electrochromic compounds $RED_1$ and $OX_2$ and/or mixtures thereof, any desired monochromic hues can be established. For a polychromic color display, two or more such electrochromic devices can be placed flat one on top of the other, with each of these devices being capable of producing a different hue. Such a stack is preferably built up in such a way that the devices in contact with one another have a common light-transparent plate, which is then provided with a conductive coating on both sides and, depending on the design, divided into segments. A stack then consists, for example, of three electrochromic devices consisting of at least four plates. By switching on segments in various of these stacked devices, multicolored displays can be achieved. If consecutive segments in different devices of this kind are switched on, mixed colors are obtained. Thus, any desired colors can be displayed in the context of trichromicity, i.e., for example, colored images.

Preference is given to electrochromic devices according to the invention which comprise an oxidizable substance $RED_1$ of the formulas (CC) to (CCIII) and a reducible substance $OX_2$ and, if desired, further oxidizable and/or reducible substances, where (a) the reducible substance has at least one (preferably at least two) chemically reversible reduction waves in the cyclic voltammogram and the oxidizable substance correspondingly has at least one (preferably at least two) chemically reversible oxidation waves, or (b) the reducible substance and the oxidizable substance are covalently bonded to one another via a bridge B, or (c) the reducible and/or oxidizable substances selected are those in which the reversible transition between the oxidizable form and the reducible form or vice versa is associated with the breaking or forming of a σ bond, or

(d) the reducible substance and/or the oxidizable substance are metal salts or metal complexes of metals which exist in at least two oxidation states, or

(e) the reducible and/or oxidizable substances are oligomers and polymers containing at least one of said redox systems, but also pairs of such redox systems as defined under (a) to (d), or the reducible and/or oxidizable substance employed is a mixture of the substances described in (a) to (e).

Suitable $OX_2$ and further $RED_1$ for the purposes of the invention are substances which, on reduction or oxidation at the cathode or anode in the solvent mentioned, give products $RED_2$ and $OX_1$ which do not undergo any subsequent chemical reaction, but instead can be fully oxidized or reduced back to $OX_2$ and $RED_1$.

Suitable reducible substances $OX_2$ are, for example:

(I)

(II)

(III)

(IV)

(V)

(VI)

(VII)

(VIII)

-continued (IX)

(X)

(XI)

(XII)

(CI)

(CII)

(CIII)

and

-continued (CIV)

in which

R² to R⁵, R⁸, R⁹, R¹⁶ to R¹⁹, independently of one another, are $C_1$–$C_{18}$-alkyl, $C_2$–$C_{12}$-alkenyl, $C_4$–$C_7$-cycloalkyl, $C_7$–$C_{15}$-aralkyl, or $C_6$–$C_{10}$-aryl, or R⁴; R⁵ or R⁸; R⁹ together can form a —(CH₂)₂— or —(CH₂)₃— bridge, R⁶, R⁷ and R²² to R²⁵, independently of one another, are hydrogen, $C_1$–$C_4$-alkyl, $C_1$–$C_4$-alkoxy, halogen, cyano, nitro, or $C_1$–$C_4$-alkoxycarbonyl, or R²²; R²³ and/or R²⁴; R²⁵ can form a —CH=CH—CH=CH— bridge, R¹⁰; R¹¹, R¹⁰; R¹³, R¹²; R¹³ and R¹⁴; R¹⁵, independently of one another, are hydrogen or in pairs are a —(CH₂)₂—, —(CH₂)₃—, or —CH=CH— bridge, R²⁰ and R²¹, independently of one another, are O, N—CN, C(CN)₂, or N—$C_6$–$C_{10}$-aryl, R²⁶ and R²⁷ are hydrogen, $C_1$–$C_4$-alkyl, $C_1$–$C_4$-alkoxy, halogen, cyano, nitro, $C_1$–$C_4$-alkoxycarbonyl, or $C_6$–$C_{10}$-aryl, R⁶⁹ to R⁷⁴, R⁸⁰ and R⁸¹, independently of one another, are hydrogen or $C_1$–$C_6$-alkyl, or R⁶⁹; R¹², R⁷⁰; R¹³, R⁷³; R⁸⁰ and/or R⁷⁴; R⁸¹ together form a —CH=CH—CH=CH— bridge, E¹ and E², independently of one another, are O, S, NR¹, or C(CH₃)₂, or E¹ and E² together form an —N—(CH₂)₂—N— bridge, R¹ is $C_1$–$C_{18}$-alkyl, $C_2$–$C_{12}$-alkenyl, $C_4$–$C_7$-cycloalkyl, $C_7$–$C_{15}$-aralkyl, or $C_6$–$C_{10}$-aryl, Z¹ is a direct bond or —CH=CH—, —C(CH₃)=CH—, —C(CN)=CH—, —CCl=CCl—, —C(OH)=CH—, —CCl=CH—, —C≡C—, —CH=N—N=CH—, —C(CH₃)=N—N=C(CH₃)—, or —CCl=N—N=CCl—,

Z² is —(CH₂)$_r$— or —CH₂—C₆H₄—CH₂—, r is an integer from 1 to 10,

R⁹⁴ and R⁹⁵, independently of one another, are hydrogen or cyano,

R¹⁰¹ to R¹⁰⁵, independently of one another, are $C_6$–$C_{10}$-aryl or an optionally benzo-fused aromatic or quasi-aromatic, five- or six-membered heterocyclic ring, R¹⁰⁷, R¹⁰⁹, R¹¹³ and R¹¹⁴, independently of one another, are a radical of the formulas (CV) to (CVII)

(CV)

-continued (CVI)

(CVII)

$R^{108}$, $R^{115}$ and $R^{116}$, independently of one another, are $C_6$–$C_{10}$-aryl or a radical of the formula (CV), $R^{110}$ to $R^{112}$, $R^{117}$ and $R^{118}$, independently of one another, are hydrogen, $C_1$- to $C_4$-alkyl, halogen, or cyano, $E^{101}$ and $E^{102}$, independently of one another, are O, S, or N—$R^{119}$, $R^{119}$ and $R^{122}$, independently of one another, are $C_1$–$C_{18}$-alkyl, $C_2$–$C_8$-alkenyl, $C_4$–$C_7$-cycloalkyl, $C_7$–$C_{15}$-aralkyl, or $C_6$–$C_{10}$-aryl,

$R^{106}$, $R^{120}$, $R^{121}$, $R^{123}$ and $R^{124}$, independently of one another, are hydrogen, $C_1$–$C_4$-alkyl, $C_1$–$C_4$-alkoxy, halogen, cyano, nitro, or $C_1$–$C_4$-alkoxycarbonyl, or

$R^{120}$, $R^{121}$ or $R^{123}$, $R^{124}$ together form a —CH=CH—CH=CH— bridge,

$A^1$, $A^2$ and $A^3$, independently of one another, are O or $C(CN)_2$,

$R^{96}$ is hydrogen, phenyl, or tert-butyl, and

X⁻ is an anion which is redox-inert under the conditions. Examples of suitable oxidizable substances $RED_1$ are the following:

(XX)

(XXI)

(XXII)

(XXIII)

(XXIV)

(XXV)

(XXVI)

(XXVII)

(XXVIII)

(XXIX)

(XXX)

-continued (XXXI)

(XXXII)

and (XXXIII)

in which
R$^{28}$ to R$^{31}$, R$^{34}$, R$^{35}$, R$^{38}$, R$^{39}$, R$^{46}$, R$^{53}$ and R$^{54}$, independently of one another, are C$_1$–C$_{18}$-alkyl, C$_2$–C$_{12}$-alkenyl, C$_4$–C$_7$-cycloalkyl, C$_7$–C$_{15}$-aralkyl, or C$_6$–C$_{10}$-aryl, R$^{32}$, R$^{33}$, R$^{36}$, R$^{37}$, R$^{40}$, R$^{41}$, R$^{42}$ to R$^{45}$, R$^{47}$, R$^{48}$, R$^{49}$ to R$^{58}$, independently of one another, are hydrogen, C$_1$–C$_4$-alkyl, C$_1$–C$_4$-alkoxy, halogen, cyano, nitro, C$_1$–C$_4$-alkoxycarbonyl, or C$_6$–C$_{10}$-aryl, and R$^{57}$ and R$^{58}$ are additionally an aromatic or quasi-aromatic, five- or six-membered heterocyclic ring which is optionally benzo-fused, and R$^{48}$ is additionally NR$^{75}$R$^{76}$, or R$^{49}$; R$^{50}$ and/or R$^{51}$; R$^{52}$ form a —(CH$_2$)$_3$—, —(CH$_2$)$_4$—, —(CH$_2$)$_5$—, or —CH=CH—CH=CH— bridge, Z$^3$ is a direct bond, a —CH=CH—, or —N=N— bridge, =Z$^4$= is a direct double bond, a =CH—CH=, or =N—N= bridge, E$^3$ to E$^5$, E$^{10}$ and E$^{11}$, independently of one another, are O, S, NR$^{59}$, or C(CH$_3$)$_2$, and E$^5$ is additionally C=O or SO$_2$, E$^3$ and E$^4$, independently of one another, can additionally be —CH=CH—, E$^6$ to E$^9$, independently of one another, are S, Se, or NR$^{59}$, R$^{59}$, R$^{75}$ and R$^{76}$, independently of one another, are C$_1$–C$_{12}$-alkyl, C$_1$–C$_{10}$-alkenyl, C$_4$–C$_7$-cycloalkyl, C$_7$–C$_{15}$-aralkyl, or C$_6$–C$_{10}$-aryl, and R$^{75}$ is additionally hydrogen or R$^{75}$ and R$^{76}$ in the definition of NR$^{75}$R$^{76}$ are, together with the N atom to which they are bonded, a five- or six-membered ring, which optionally contains further heteroatoms, R$^{61}$ to R$^{68}$, independently of one another, are hydrogen, C$_1$–C$_6$-alkyl, C$_1$–C$_4$-alkoxy, cyano, C$_1$–C$_4$-alkoxycarbonyl, or C$_6$–C$_{10}$-aryl, and R$^{61}$; R$^{62}$ and R$^{67}$; R$^{68}$, independently of one another, additionally form a —(CH$_2$)$_3$—, —(CH$_2$)$_4$—, or —CH=CH—CH=CH— bridge, or R$^{62}$; R$^{63}$; R$^{64}$; R$^{65}$ and R$^{66}$; R$^{67}$ form a —O—CH$_2$CH$_2$—O— or —O—CH$_2$CH$_2$CH$_2$—O— bridge, v is an integer between 0 and 100, R$^{82}$, R$^{83}$, R$^{88}$ and R$^{89}$, independently of one another, are C$_1$–C$_{18}$-alkyl, C$_2$–C$_{12}$-alkenyl, C$_4$–C$_7$-cycloalkyl, C$_7$–C$_{15}$-aralkyl, or C$_6$–C$_{10}$-aryl, R$^{84}$ to R$^{87}$ and R$^{90}$ to R$^{93}$, independently of one another, are hydrogen or C$_1$–C$_6$-alkyl, or R$^{84}$; R$^{86}$, R$^{85}$; R$^{87}$, R$^{90}$; R$^{92}$ and/or R$^{91}$; R$^{93}$ together form a —CH=CH—CH=CH— bridge.

Also suitable as RED$_1$ are anions, such as, for example, I$^-$, I$_3^-$, Br$^-$, and SCN$^-$.

Examples of optionally oligomeric or polymeric redox systems linked via a bridge B are those of the formula $$Y-[-(-B-Z-)_a-(-B-Y-)_b-]_c-B-Z \quad (L),$$

in which
Y and Z, independently of one another, are an OX$_2$ or RED$_1$ radical, where either at least one Y is OX$_2$ and at least one Z is RED$_1$ or Y and Z are OX$_2$, where OX$_2$ is the radical of a reversibly electrochemically reducible redox system, and RED$_1$ is the radical of a reversibly electrochemically oxidizable redox system, B is a bridging unit, c is an integer from 0 to 1000, and a and b, independently of one another, are integers from 0 to 100.

(a+b)·c is preferably ≦10,000.

The term reversibly electrochemically reducible or oxidizable here is taken to mean that electron transfer can take place with or without a change in the σ structure entirely within the sense of the above-mentioned definition of OX$_2$ and RED$_1$ according to the invention.

The electrochromic compounds of the formula (L) are in particular taken to mean those of the formulas $$OX_2—B\text{-}RED_1, \quad (La)$$

$$OX_2—B\text{-}RED_1\text{-}B—OX_2, \quad (Lb)$$

$$RED_1\text{-}B—OX_2—B\text{-}RED_1, \quad (Lc)$$

$$OX_2—(B\text{-}RED_1\text{-}B—OX_2)_d—B\text{-}RED_1, \quad (Ld)$$

or $$OX_2—(B—OX_2)_e—B—OX_2 \quad (Le)$$

in which
OX$_2$, RED$_1$ and B are as defined above, d is an integer from 1 to 5, and e is an integer from 0 to 5.

OX$_2$ and RED$_1$ in the formulas (L) and (La) to (Le) are taken to mean, in particular, radicals of the above-described redox systems of the formulas (I) to (X), (CI) to (CIV), and (XX) to (XXXIII) in which the bonding to the bridging unit B takes place via one of the radicals R$^2$ to R$^{19}$, R$^{22}$ to R$^{27}$, R$^{28}$ to R$^{58}$, R$^{61}$, R$^{62}$, R$^{67}$, R$^{68}$, R$^{83}$, R$^{88}$, or R$^{122}$ or, where one of the radicals E$^1$ or E$^2$ is NR$^1$ or one of the radicals E$^3$ to E$^{11}$ is NR$^{59}$ or one of the radicals E$^{101}$ to E$^{102}$ is NR$^{119}$, takes place via R$^1$, R$^{59}$, or R$^{119}$, and said radicals are then a direct bond, and B is a bridge of the formula —$(CH_2)_m$— or —$[Y^1{}_o(CH_2)_n$—$Y^2]_o$—$(CH_2)_p$—$Y^3{}_q$—, which may be substituted by $C_1$–$C_4$-alkyl, $C_1$–$C_4$-alkoxy, halogen or phenyl, $Y^1$ to $Y^3$, independently of one another, are O, S, $NR^{60}$, COO, CONH, NHCONH, cyclopentanediyl, cyclohexanediyl, phenylene, or naphthylene, $R^{60}$ is $C_1$–$C_6$-alkyl, $C_2$–$C_6$-alkenyl, $C_4$–$C_7$-cycloalkyl, $C_7$–$C_{15}$-aralkyl, or $C_6$–$C_{10}$-aryl, n is an integer from 1 to 12, m and p, independently of one another, are integers from 0 to 8, o is an integer from 0 to 6, and q and s, independently of one another, are 0 or 1.

$OX_2$ and $RED_1$ in the formulas (L) and (La) to (Le) are very particularly taken to mean radicals of the above-described redox systems of the formulas (I), (V), (XX), (XXII), (XXIII), (XXV), (XXVI), and (XXXIII).

In another type of oligomeric or polymeric system, the $OX_2$ and/or $RED_1$ groups can also be bonded with a main group, for example, as side chains, for example, to a poly(meth)acrylate, silicone, polycarbonate, polyurethane, polyurea, polyester, polyamide, cellulose, or other oligomeric or polymeric systems.

Examples of metal salts or metal complexes which can be employed as $OX_2$ or $RED_1$ are $Fe^{3+/2+}$, $Ni^{3+/2+}$, $Co^{3+/2+}$, $Cu^{2+/+}$, $[Fe(CN)_6]^{3-/4-}$, $Fe_4[Fe(CN)_6]_3{}^{0/4-}$, $[Co(CN)_6]^{3-/4-}$, $[Fe(cyclopentadienyl)_2]^{0/+}$, $Lu(Pc)^{2+to\ 2-}$ (where Pc is phthalocyanine), and $Fe[Fe(CN)_6]^{0/1-}$.

Suitable counterions for metal ions and cationic complexes are all redox-inert anions $X^-$, as described more precisely later, and suitable counterions of the anionic complexes are all redox-inert cations $M'^+$, for example, alkali metals or quaternary ammonium salts, such as $Na^+$, $K^+$, $N(CH_3)_4{}^+$, $N(C_4H_9)_4{}^+$, and $C_6H_5CH_2N(CH_3)_3{}^+$, and others.

Preference is likewise given to an electrochromic device containing mixtures of the electrochromic substances mentioned above in general and preferred terms. Examples of such mixtures are (I)+(CI)+(CC), (I)+(IV)+(CC)+(XXII), (La)+(I)+(CC)+(XXVI), without this being intended to express any restriction.

The mixing ratios are variable within broad limits. They allow a desired hue or degree of blackness to be optimized and/or the desired dynamics of the device to be optimized.

In the substituent definitions given above, alkyl radicals, including derivatives, are, for example, alkoxy or aralkyl radicals, preferably those having 1 to 12 C atoms, in particular having 1 to 8 C atoms, unless stated otherwise. They can be straight-chain or branched and can optionally carry further substituents, such as $C_1$–$C_4$-alkoxy, fluorine, chlorine, hydroxyl, cyano, $C_1$–$C_4$-alkoxycarbonyl, or COOH.

The term cycloalkyl radicals is preferably taken to mean those having 3 to 7 carbon atoms, in particular having 5 or 6 carbon atoms.

Alkenyl radicals are preferably those having from 2 to 8 carbon atoms, in particular 2 to 4 carbon atoms.

Aryl radicals, including those in aralkyl radicals, are phenyl or naphthyl radicals, in particular phenyl radicals. They can be substituted by 1 to 3 of the following radicals: $C_1$–$C_6$-alkyl, $C_1$–$C_6$-alkoxy, fluorine, chlorine, bromine, cyano, hydroxyl, $C_1$–$C_6$-alkoxycarbonyl, or nitro. Two adjacent radicals can also form a ring.

The term optionally benzo-fused aromatic or quasi-aromatic, five- or six-membered heterocyclic rings is taken to mean, in particular, imidazole, benzimidazole, oxazole, benzoxazole, thiazole, benzothiazole, indole, pyrazole, triazole, thiophene, isothiazole, benzisothiazole, 1,3,4- or 1,2,4-thiadiazole, pyridine, quinoline, pyrimidine, and pyrazine. They may be substituted by 1 to 3 of the following radicals: $C_1$–$C_6$-alkyl, $C_1$–$C_6$-alkoxy, fluorine, chlorine, bromine, cyano, nitro, hydroxyl, mono- or di-$C_1$–$C_6$-alkylamino, $C_1$–$C_6$-alkoxycarbonyl, $C_1$–$C_6$-alkylsulfonyl, $C_1$–$C_6$-alkanoylamino, phenyl, or naphthyl. Two adjacent radicals may also form a ring.

The electrochromic substances are either known (e.g., *Topics in Current Chemistry*, Vol. 92, pages 1–44, (1980), *Angew. Chem.*, 90, 927 (1978), *Adv. Mater.*, 3, 225, (1991), German Offenlegungsschrift 3,917,323, *J. Am. Chem. Soc.*, 117, 8528 (1995), *J. C. S., Perkin II*, 1990, 1777, German Offenlegungsschrift 4,435,21 1, EP-A 476,456, EP-A 476,457, German Offenlegungsschrift 4,007,058, *J. Org. Chem.*, 57, 1849 (1992), and *J. Am. Chem. Soc.*, 99, 6120, 6122 (1977)) or can be prepared analogously. The compounds of the formula (L) are likewise known. E.g., WO 97/30134.

Synthetically required ions, such as bromide, are subsequently replaced by redoxinert ions.

Besides the oxidizable compounds of the formula (CC) or (CCII) according to the invention, particular preference is given to the reducible electrochromic compounds of the formulas (I), (II), (III), (IV), and (V).

Besides the oxidizable compounds of the formula (CC) or (CCII) according to the invention, very particular preference is given to the reducible electrochromic compounds of the formulas (I), (IV) and (V)

in which $R^2$, $R^3$, $R^8$ and $R^9$, independently of one another, are methyl, ethyl, propyl, butyl, pentyl, hexyl, heptyl, benzyl, phenethyl, phenylpropyl, phenyl, 2-methylphenyl, or 2,6-dimethylphenyl or $R^8$ and $R^9$ together form a —$(CH_2)_2$— or —$(CH_2)_3$— bridge, $R^{10}$ to $R^{15}$ are hydrogen, $R^{69}$ to $R^{73}$, $R^{80}$ and $R^{81}$, independently of one another, are hydrogen or methyl, or $R^{12}$; $R^{69}$, $R^{13}$; $R^{70}$, $R^{73}$; $R^{80}$ and/or $R^{74}$; $R^{81}$ form a —CH=CH—CH=CH— bridge, $Z_1$ is a direct bond or —CH=CH—, and $X^-$ is an anion which is redox-inert under the conditions, where the alkyl radicals may be branched, for example 2-butyl and 1-phenyl-2-propyl.

Very outstandingly suitable for the purposes of the invention are the electrochromic compounds of the formula (I) in which $R^2$ and $R^3$ are identical and are methyl, ethyl, butyl, heptyl, or phenylpropyl, $R^{12}$ to $R^{15}$ and $R^{69}$ to $R^{72}$ are hydrogen, $Z^1$ is a direct bond, and $X^-$ is a redox-inert anion or $I^-$.

The light-protected electrochromic device according to the invention preferably contains, in its electrochromic medium, at least one solvent in which the electrochromic substances, if used with a conductive salt and if used with further additives, are dissolved. The solvent can also have been thickened in the form of a gel, for example by polyelectrolytes, porous solids or nanoparticles having large active surface areas.

Suitable solvents are all solvents which are redox-inert under the selected voltages and which cannot eliminate electrophiles or nucleophiles or themselves react as sufficiently strong electrophiles or nucleophiles and thus could react with the colored free-radical ions. Examples are propylene carbonate, γ-butyrolactone, acetonitrile, propionitrile, benzonitrile, glutaronitrile, methylglutaronitrile, 3,3'-oxydipropionitrile, hydroxypropionitrile, dimethylformamide, N-methylpyrrolidone, sulfolane, 3-methylsulfolane, or mixtures thereof. Preference is given to propylene carbonate, benzonitrile, and mixtures with one another or with glutaronitrile or 3-methylsulfolane. Particular preference is given to propylene carbonate. Particular preference is likewise given to benzonitrile.

The electrochromic solution can contain at least one inert conductive salt. In particular if at least one of the substances of the redox pair $RED_1/OX_2$ is of an ionic nature, the addition of a conductive salt, can be omitted.

Suitable inert conductive salts are lithium, sodium and tetraalkylammonium salts, in particular the latter. The alkyl groups can contain between 1 and 18 carbon atoms and can be identical or different. Preference is given to tetrabutylammonium. Suitable anions for these salts, in particular as anions $X^-$ in the formulas (I) to (VI), (CI), (CII) and (CV) to (CVII) and in the metal salts, are all redox-inert, colorless anions.

Examples are tetrafluoroborate, tetraphenylborate, cyanotriphenylborate, tetramethoxyborate, tetrapropoxyborate, tetraphenoxyborate, perchlorate, chloride, nitrate, sulfate, phosphate, methanesulfonate, ethanesulfonate, tetradecanesulfonate, pentadecanesulfonate, trifluoromethanesulfonate, perfluorobutanesulfonate, perfluorooctanesulfonate, benzenesulfonate, chlorobenzenesulfonate, toluenesulfonate, butylbenzenesulfonate, tert-butylbenzenesulfonate, dodecylbenzenesulfonate, trifluoromethylbenzenesulfonate, hexafluorophosphate, hexafluoroarsenate, hexafluorosilicate, or 7,8- or 7,9-dicarbanido-undecaborate(-1) or (-2), which are optionally substituted on the B and/or C atoms by one or two methyl, ethyl, butyl or phenyl groups, dodecahydrodicarbadodecaborate(-2) or B-methyl-C-phenyl-dodecahydrodicarbadodecaborate(-1).

Likewise suitable, including as anions $X^-$ in the formulas (I) to (VI), (CI), (CII) and (CV) to (CVII) and in the metal salts, are the above-mentioned anions which can also take on the role of an $RED_1$, for example, $I^-$ and $I_3^-$.

The conductive salts are preferably employed in the range from 0 to 1 mol/l.

Further additives which can be employed are thickeners in order to control the viscosity of the electroactive solution. This can be of importance for avoiding segregation, i.e. the formation of colored streaks or spots on extended operation of the electrochromic device in the switched-on state, and for controlling the fading rate after the current is switched off.

Suitable thickeners are all compounds usual for this purpose, such as, for example, polyacrylate, polymethacrylate (Luctite L®), polycarbonate, or polyurethane.

Suitable further additives for the electrochromic solution for the desired protection against UV light (<350 nm) from case to case are UV absorbers. Examples are UVINUL® 3000 (2,4-dihydroxybenzophenone, BASF), SANDUVOR® 3035 (2-hydroxy-4-n-octyloxybenzophenone, Clariant), Tinuvin® 571 (2-(2H-benzotriazol-2-yl)-6-dodecyl-4-methylphenol, Ciba), Cyasorb 24™ (2,2'-dihydroxy-4-methoxybenzophenone, American Cyanamid Company), UVINUL® 3035 (ethyl 2-cyano-3,3-diphenylacrylate, BASF), UVINUL® 3039 (2-ethylhexyl 2-cyano-3,3-diphenylacrylate, BASF), UVINUL® 3088 (2-ethylhexyl p-methoxycinnamate, BASF), and CHIMASSORB® 90 (2-hydroxy-4-methoxy-benzophenone, Ciba). Preference is given to the four last-mentioned compounds. Preference is likewise given to mixtures of UV absorbers, for example, of the four last-mentioned compounds. Particular preference is given to the mixture of UVINUL® 3039 and CHIMASSORB® 90.

The UV absorbers are employed in the range from 0.01 to 2 mol/l, preferably from 0.04 to 1 mol/l.

The electrochromic solution contains the electrochromic substances $OX_2$ and $RED_1$, in particular those of the formulas (I) to (X) and (CC) and/or (CCII), in each case in a concentration of at least $10^{-4}$ mol/l (preferably from 0.001 to 0.5 mol/l). The total concentration of all electrochromic substances present is preferably less than 1 mol/l.

In order to operate the electrochromic device according to the invention, a constant, pulsed or amplitude-varying, for example, sinusoidal, direct current is used. The voltage depends on the desired color depth, but in particular on the reduction or oxidation potentials of the $OX_2$ and $RED_1$ used. Such potentials can be found, for example, in *Topics in Current Chemistry*, Volume 92, pp. 1–44, (1980) or *Angew. Chem.*, 90, 927 (1978) or in the references cited therein. The difference in their potentials is a guide for the requisite voltage, but the electrochromic device can be operated at lower or higher voltage. In many cases, for example on use of $OX_2$ of formula (I) or (V) and $RED_1$ of formula (CC), this potential difference necessary for operation is $\leq 1$ V. Such electrochromic devices can therefore be supplied in a simple manner with the current from photovoltaic silicon cells.

If the voltage is switched off, the electrochromic device according to the invention returns to its original state. This erasing can be considerably accelerated if the contacted segments or plates are short-circuited. The display can also be erased very rapidly by repeated reversal of the voltage, optionally also with simultaneous reduction in the voltage.

By varying the layer thickness of the electrochromic device, the viscosity of the electrochromic solution and/or the diffusibility or driftability of the electrochromic substances, the switch-on and switch-off times of the display device can be modified within broad limits. Thus, for example, thin layers exhibit shorter switching times than thick layers. It is thus possible to construct fast- and slow-switchable devices and thus to match them to the particular applications in an optimum manner.

In slow devices, in particular display devices, a power-saving or refresh mode can be used in the switched-on state in order to maintain the displayed information. After the information to be displayed has been built up, for example by direct voltage of sufficient level which is constant or varying with high frequency or pulsed, the voltage is switched to pulsed or varying direct voltage of low frequency, with the contacting of the segments not being short-circuited during the phases in which the voltage is zero. This low frequency can be, for example, in the region of 1 Hz or lower, while the durations of the switch-on and switch-off phases need not be of equal lengths, but instead, for example, the switch-off phases can be significantly longer. Since the color depth of the displayed information drops only slowly during the current pauses in the non-short-circuited state, relatively short current pulses are sufficient to compensate for these losses again in the subsequent refresh phase. In this way, a flicker-free image with virtually constant color depth is obtained, but its maintenance requires only a fraction of the current that would arise in the case of permanent current flow.

Specific embodiments of the above-mentioned types 1 and 2 can be, for example, the following, which are likewise the subject-matter of the invention if they comprise the electrochromic substances according to the invention.

Type 1: (non-mirrored)

From the light protection/light filter area: window panes for buildings, road vehicles, aircraft, railways, ships, roof glazing, automobile sunroofs, glazing of greenhouses and conservatories, light filters of any desired type;

From the security/confidentiality area: separating panes for room dividers in offices, road vehicles, aircraft, railways, sight protection screens, for example at bank counters, door glazing, visors for motorcycle or pilot helmets;

From the design area: glazing of ovens, microwave equipment, other domestic appliances, furniture;

From the display area: analogue voltage displays, as battery testers, tank displays, and temperature displays.

Type 1: (mirrored)

Mirrors of all types for road vehicles, railways, in particular, planar, spherical, aspherical mirrors, and combinations thereof, such as spherical/aspherical mirror glazing in furniture.

Type 2:

Display devices of all types, segment or matrix displays for watches, computers, electrical equipment, electronic equipment, such as radios, amplifiers, TV sets, CD players, destination displays in buses and trains, departure displays in stations and airports, flat screens, and all applications mentioned under types 1 and 2 which contain at least one switchable static or variable display device, such as separating screens containing displays such as "Please do not disturb", "Counter closed", for example, automobile mirrors containing displays of any desired type, such as display of the temperature, faults in the vehicle, for example, oil temperature, open doors, time, compass direction.

The invention furthermore relates to dihydrophenazines of the formulas (CC) in which
- $R^{201}$ is aryl (particularly $C_6$–$C_{10}$-aryl),
- $R^{202}$ is $C_2$–$C_{12}$-alkyl, $C_3$–$C_7$-cycloalkyl, $C_2$–$C_{12}$-alkenyl, or $C_7$–$C_{16}$-aralkyl,
- $R^{203}$ and $R^{204}$, independently of one another, are hydrogen, halogen, $C_1$–$C_4$-alkyl, $C_1$–$C_4$-alkoxy, cyano, or $C_6$–$C_{10}$-aryl,
- m and n, independently of one another, are integers from 1 to 4, or
- two adjacent $R^{203}$ and $R^{204}$, independently of one another, are a bivalent —CH=CH—CH=CH— radical if m or n is at least 2.

In particular in dihydrophenazines of the formulas (CC),
- $R^{201}$ is phenyl, which can optionally carry up to three methyl, methoxy, chlorine, bromine, or cyano radicals,
- $R^{202}$ is optionally branched $C_2$–$C_8$-alkyl, cyclopentyl, cyclohexyl, benzyl, phenethyl, or phenylpropyl,
- $R^{203}$ and $R^{204}$, independently of one another, are hydrogen, chlorine, bromine, methyl, ethyl, propyl, butyl, methoxy, ethoxy, cyano, or phenyl,
- m and n, independently of one another, are integers from 1 to 2, or
- two adjacent $R^{203}$ and $R^{204}$, independently of one another, are a bivalent —CH=CH—CH=CH— radical if m or n is 2.

Very particularly in dihydrophenazines of the formula (CC),
- $R^{201}$ is phenyl,
- $R^{202}$ is ethyl, propyl, butyl, phenylethyl, or phenylpropyl,
- $R^{203}$ and $R^{204}$ are hydrogen, and
- m and n are 1.

The invention furthermore relates to dihydrophenazines of the formula (CCII) in which
- $R^{202}$ is alkyl, cycloalkyl, alkenyl, aralkyl, or aryl, particularly $C_1$–$C_{12}$-alkyl, $C_3$–$C_7$-cycloalkyl, $C_2$–$C_{12}$-alkenyl, $C_7$–$C_{16}$-aralkyl, or $C_6$–$C_{10}$-aryl,
- B is a bivalent bridge, particularly —$(CH_2)_p$—, —$(CH_2)$—$(O$—$CH_2)$—$(O$—$CH_2)_q$—$O$—$CH_2$—, or —$(CH_2)_r$—$C_6H_4$—$(CH_2)_s$—, where the $CH_2$ groups may be substituted by methyl,
- $R^{203}$ and $R^{204}$, independently of one another, are hydrogen, halogen, $C_1$–$C_4$-alkyl, $C_1$–$C_4$-alkoxy, cyano, or $C_6$–$C_{10}$-aryl,
- m and n, independently of one another, are integers from 1 to 4, or two adjacent $R^{203}$ and $R^{204}$, independently of one another, are a bivalent —CH=CH—CH=CH— radical if m or n is at least 2,
- p is an integer from 2 to 20, and
- q, r, and s, independently of one another, are integers from 0 to 10.

In particular in dihydrophenazines of the formula (CCII),
- $R^{202}$ is optionally branched $C_2$–$C_8$-alkyl, cyclopentyl, cyclohexyl, benzyl, phenethyl, phenylpropyl, or phenyl, where these radicals can optionally carry up to three methyl, methoxy, chlorine, bromine, or cyano radicals,
- B is —$(CH_2)_p$—,
- $R^{203}$ and $R^{204}$, independently of one another, are hydrogen, chlorine, bromine, methyl, ethyl, propyl, butyl, methoxy, ethoxy, cyano, or phenyl,
- m and n, independently of one another, are integers from 1 to 2, or two adjacent $R^{203}$ and $R^{204}$, independently of one another, are a bivalent —CH=CH—CH=CH— radical if m or n is 2, and
- p is an integer from 2 to 10.

Very particularly in dihydrophenazines of the formula (CCII),
- $R^{202}$ is methyl, ethyl, propyl, butyl, phenethyl, phenylpropyl, or phenyl,
- B is —$(CH_2)_p$—,
- $R^{203}$ and $R^{204}$ are hydrogen,
- m and n are 1, and
- p is an integer from 3 to 5.

To a very particular extent in dihydrophenazines of the formula (CCII)
- $R^{202}$ is phenyl,
- B is —$(CH_2)_p$—,
- $R^{203}$ and $R^{204}$ are hydrogen,
- m and n are 1, and
- p is 3 or 4.

The following examples further illustrate details for representative embodiments of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all percentages are percentages by weight.

EXAMPLES

Example 1

Figure 1:
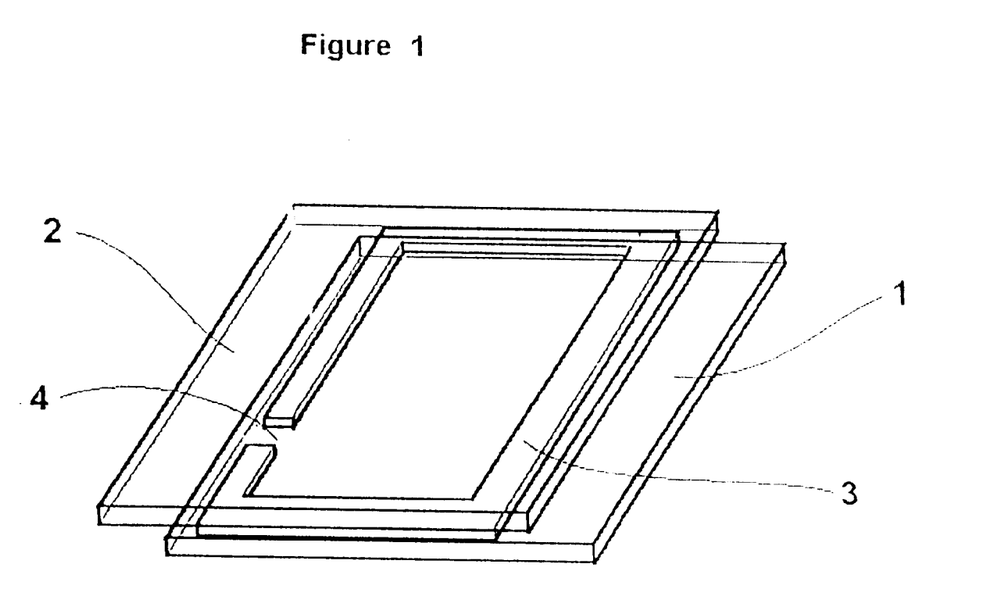
FIG. 1 shows a cell constructed according to Example 1 of the invention.

A cell was constructed as shown in FIG. 1. To this end, two glass plates 1 and 2 that were coated on one surface with ITO were used.

A mixture of 97% of photocuring DELO-Katiobond® 4594 epoxy adhesive (DELO Industrieklebstoffe, Landsberg) and 3% of glass beads having a diameter of 200 μm were applied in a ring shape (3, see FIG. 1) to the ITO-coated side of glass plate 1 in such a way that a 2 mm wide opening (4, see FIG. 1) was left. Glass plate 2 was then placed on the adhesive bead in such a way that the ITO layers of the two plates 1 and 2 faced each other and a geometry as shown in FIG. 1 was formed. The adhesive was cured by exposure for 10 minutes to daylight in the vicinity of a window and then for 20 minutes at 105° C. without exposure.

A dish was filled under a nitrogen atmosphere with a solution which was 0.02 molar with respect to the electrochromic compounds of the formulas

(CCC)

and

(CCCI)

and 0.1 molar with respect to each of the UV absorbers of the formulas (CCCX)

and (CCCXI)

in anhydrous, oxygen-free propylene carbonate.

The cell was then placed vertically in the dish under a nitrogen atmosphere in such a way that the opening 4 was located beneath the liquid level. The dish with the cell was placed in a desiccator, which was evacuated to 0.05 mbar and then carefully aerated with nitrogen. During the aeration, the electrochromic solution rose through the opening 4 into the cell and, apart from a small bubble, filled the entire volume. The cell was removed from the solution, cleaned at the opening 4 under a nitrogen atmosphere by wiping with a paper towel, and sealed with the photochemically curable acrylate adhesive DELO-Photobond® 4497 (DELO Industrieklebstoffe, Landsberg). The cell was then exposed for 1 minute under a nitrogen atmosphere with a DELOLUX® 03 lamp (DELO Industrieklebstoffe, Landsberg) at a distance of 8 cm from the opening 4, and cured at room temperature overnight under a nitrogen atmosphere.

Application of a voltage of 0.9 V to the two plates 1 and 2 caused the cell rapidly to turn a deep greenish blue. Switching off the voltage and short-circuiting the contacts caused the color rapidly to disappear again.

The following electrochromic compounds of Examples 2 to 12 were employed entirely analogously:

| Ex. | OX$_2$ | RED$_1$ |
|---|---|---|
| 2 | | |

-continued

| Ex. | OX₂ | RED₁ |
|---|---|---|
| 3 |  2 BF₄⁻ |  |
| 4 |  2 BF₄⁻ |  |
| 5 |  2 BF₄⁻ |  |
| 6 |  2 BF₄⁻ |  |
| 7 |  2 PF₆⁻ |  |

-continued

| Ex. | OX$_2$ | RED$_1$ |
|---|---|---|
| 8 |  2 BF$_4^-$ |  |
| 9 |  2 PF$_6^-$ |  |
| 10 |  2 BF$_4^-$ |  |
| 11 |  2 BF$_4^-$ |  |

| Ex. | OX$_2$ | RED$_1$ |
|---|---|---|
| 12 |  2 BF$_4^-$ |  |

What is claimed is:

1. An electrochromic device comprising

(a) a pair of glass or plastic plates or plastic films wherein at least one such plate or film is provided on one side each with an electrically conductive coating, wherein
  (1) at least one such plate or film and its conductive coating is transparent,
  (2) the other such plate or film and its conductive coating is optionally mirrored,
  (3) the electrically conductive layer of one or both of the two plates or films is optionally divided into separate segments optionally provided with individual contacts, and
  (4) the plates or films are joined on the sides of their conductive coating by means of a sealing ring to form a volume; and (b) the volume formed by the two plates or films and the sealing ring is filled with an electrochromic medium comprising a pair of electrochromic substances OX$_2$ and RED$_1$, wherein
  (1) OX$_2$ is a reducible electrochromic substance, and
  (2) RED$_1$ is an oxidizable electrochromic substance represented by at least one of the formulas (CC)

(CCI)

(CCII)

(CCIII)

wherein
R$^{201}$ is aryl,
R$^{202}$ is alkyl, cycloalkyl, alkenyl, aralkyl, or aryl,
B is a bivalent bridge,
m and n, independently of one another, are integers from 1 to 4, and
R$^{203}$ to R$^{206}$, independently of one another, are hydrogen, halogen, alkyl, alkoxy, cyano or aryl, with the provisos that when m is at least 2, two adjacent R$^{203}$ together also optionally represent a bivalent —CH=CH—CH=CH— radical and when n is at least 2, two adjacent R$^{204}$ together also optionally represent a bivalent —CH=CH—CH=CH— radical.

2. An electrochromic device according to claim 1 wherein RED$_1$ represents one of the formulas (CC), (CCI), (CCII), or (CCIII) wherein
R$^{201}$ is C$_6$–C$_{10}$-aryl, $R^{202}$ is $C_1$–$C_{12}$-alkyl, $C_3$–$C_7$-cycloalkyl, $C_2$–$C_{12}$-alkenyl, $C_7$–$C_{16}$-aralkyl, or $C_6$–$C_{10}$-aryl, B is —$(CH_2)_p$—, —$(CH_2)$—$(O$—$CH_2)_q$—$O$—$CH_2$— or —$(CH_2)_r$—$C_6H_4$—$(CH_2)_s$—, where the $CH_2$ groups may be substituted by methyl, $R^{203}$ to $R^{206}$, independently of one another, are hydrogen, halogen, $C_1$–$C_4$-alkyl, $C_1$–$C_4$-alkoxy, cyano, or $C_6$–$C_{10}$-aryl, m and n, independently of one another, are integers from 1 to 4, with the provisos that when m is at least 2, two adjacent $R^{203}$ together also optionally represent a bivalent —CH═CH—CH═CH— radical and when n is at least 2, two adjacent $R^{204}$ together also optionally represent a bivalent —CH═CH—CH═CH— radical, p is an integer from 2 to 20, and q, r, and s, independently of one another, are integers from 0 to 10.

3. An electrochromic device according to claim 1 wherein $RED_1$ represents one of the formulas (CC), (CCI), (CCII), or (CCIII) wherein $R^{201}$ is phenyl or phenyl carrying up to three methyl, methoxy, chlorine, bromine, or cyano radicals, $R^{202}$ is an optionally branched $C_1$–$C_8$-alkyl, cyclopentyl, cyclohexyl, benzyl, phenethyl, phenylpropyl radical wherein each such radical optionally carries up to three methyl, methoxy, chlorine, bromine, or cyano radicals, B is —$(CH_2)_p$—, $R^{203}$ to $R^{206}$, independently of one another, are hydrogen, chlorine, bromine, methyl, ethyl, propyl, butyl, methoxy, ethoxy, cyano, or phenyl, m and n, independently of one another, are integers from 1 to 2, with the provisos that when m is at least 2, two adjacent $R^{203}$ together also optionally represent a bivalent —CH═CH—CH═CH— radical and when n is at least 2, two adjacent $R^{204}$ together also optionally represent a bivalent —CH═CH—CH═CH— radical, and p is an integer from 2 to 10.

4. An electrochromic device according to claim 1 wherein $RED_1$ represents the formula (CC) wherein $R^{201}$ is phenyl, $R^{202}$ is methyl, ethyl, propyl, butyl, phenylpropyl, or phenyl, $R^{203}$ and $R^{204}$ are hydrogen, and m and n are 1.

5. An electrochromic device according to claim 4 wherein $R^{201}$ and $R^{202}$ are phenyl.

6. An electrochromic device according to claim 1 wherein $RED_1$ represents the formula (CCII) wherein $R^{202}$ is phenyl, B is —$(CH_2)_p$—,

$R^{203}$ and $R^{204}$ are hydrogen, m and n are 1, and p is an integer from 2 to 6.

7. An electrochromic device according to claim 6 wherein p is 3 to 5.

8. An electrochromic device according to claim 1 wherein $OX_2$ comprises a compound selected from the formulas (I)

(II)

(III)

(IV)

(V)

(VI)

(VII)

(VIII)

-continued

(IX)

(X)

(XI)

(XII)

(CI)

(CII)

(CIII)
 and

-continued (CIV)

wherein $R^2$ to $R^5$, $R^8$, $R^9$, $R^{16}$ to $R^{19}$, independently of one another, are $C_1$–$C_{18}$-alkl, $C_2$–$C_{12}$-alkenyl, $C_4$–$C_7$-cycloalkyl, $C_7$–$C_{15}$-aralkyl, or $C_6$–$C_{10}$-aryl, or $R^4$; $R^5$ or $R^8$; $R^9$ together can form a —(CH$_2$)$_2$— or —(CH$_2$)$_3$— bridge, $R^6$, $R^7$ and $R^{22}$ to $R^{25}$, independently of one another, are hydrogen, $C_1$–$C_4$-alkyl, $C_1$–$C_4$-alkoxy, halogen, cyano, nitro, or $C_1$–$C_4$-alkoxycarbonyl, or $R^{22}$; $R^{23}$ and/or $R^{24}$; $R^{25}$ can form a —CH=CH—CH=CH— bridge, $R^{10}$; $R^{11}$, $R^{10}$; $R^{13}$, $R^{12}$; $R^{13}$ and $R^{14}$; $R^{15}$, independently of one another, are hydrogen or in pairs are a —(CH$_2$)$_2$—, —(CH$_2$)$_3$—, or —CH=CH— bridge, $R^{20}$ and $R^{21}$, independently of one another, are O, N—CN, C(CN)$_2$, or N—$C_6$–$C_{10}$-aryl, $R^{26}$ and $R^{27}$ are hydrogen, $C_1$–$C_4$-alkyl, $C_1$–$C_4$-alkoxy, halogen, cyano, nitro, $C_1$–$C_4$-alkoxycarbonyl, or $C_6$–$C_{10}$-aryl, $R^{69}$ to $R^{74}$, $R^{80}$ and $R^{81}$, independently of one another, are hydrogen or $C_1$–$C_6$-alkyl, or $R^{69}$; $R^{12}$, $R^{70}$; $R^{13}$, $R^{73}$; $R^{80}$ and/or $R^{74}$; $R^{81}$ together form a —CH=CH—CH=CH— bridge, $E^1$ and $E^2$, independently of one another, are O, S, NR$^1$, or C(CH$_3$)$_2$, or $E^1$ and $E^2$ together form an —N—(CH$_2$)$_2$—N— bridge, $R^1$ is $C_1$–$C_{18}$-alkyl, $C_2$–$C_{12}$-alkenyl, $C_4$–$C_7$-cycloalkyl, $C_7$–$C_{15}$-aralkyl, or $C_6$–$C_{10}$-aryl, $Z^1$ is a direct bond or —CH=CH—, —C(CH$_3$)=CH—, —C(CN)=CH—, —CCl=CCl—, —C(OH)=CH—, —CCl=CH—, —C≡C—, —CH=N—N=CH—, —C(CH$_3$)=N—N=C(CH$_3$)—, or —CCl=N—N=CCl—,

$Z^2$ is —(CH$_2$)$_r$— or —CH$_2$–C$_6$H$_4$–CH$_2$—, r is an integer from 1 to 10,

$R^{94}$ and $R^{95}$, independently of one another, are hydrogen or cyano,

$R^{101}$ to $R^{105}$, independently of one another, are $C_6$–$C_{10}$-aryl or an optionally benzo-fused aromatic or quasi-aromatic, five- or six-membered heterocyclic ring, $R^{107}$, $R^{109}$, $R^{113}$ and $R^{114}$, independently of one another, are a radical of the formulas (CV) to (CVII)

(CV)

-continued (CVI)

(CVII)

$R^{108}$, $R^{115}$ and $R^{116}$, independently of one another, are $C_6$–$C_{10}$-aryl or a radical of the formula (CV), $R^{110}$ to $R^{112}$, $R^{117}$ and $R^{118}$, independently of one another, are hydrogen, $C_1$- to $C_4$-alkyl, halogen, or cyano, $E^{101}$ and $E^{102}$, independently of one another, are O, S, or N—$R^{119}$, $R^{119}$ and $R^{122}$, independently of one another, are $C_1$–$C_{18}$-alkyl, $C_2$–$C_8$-alkenyl, $C_4$–$C_7$-cycloalkyl, $C_7$–$C_{15}$-aralkyl, or $C_6$–$C_{10}$-aryl, $R^{106}$, $R^{120}$, $R^{121}$, $R^{123}$ and $R^{124}$, independently of one another, are hydrogen, $C_1$–$C_4$-alkyl, $C_1$–$C_4$-alkoxy, halogen, cyano, nitro, or $C_1$–$C_4$-alkoxycarbonyl, or $R^{120}$, $R^{121}$ or $R^{123}$, $R^{124}$ together form a —CH=CH—CH=CH— bridge, $A^1$, $A^2$ and $A^3$, independently of one another, are O or $C(CN)_2$, $R^{96}$ is hydrogen, phenyl, or tert-butyl, and $X^-$ is an anion which is redox-inert under the conditions.

9. A window, separating screen, sight protection screen, glazing, roof glazing, light filter, mirror, or display device comprising an electrochromic device according to claim 1.

* * * * *